United States Patent
McKenna, Jr. et al.

(10) Patent No.: US 9,049,893 B2
(45) Date of Patent: Jun. 9, 2015

(54) DEVICE FOR SECURING A MEDICAL SENSOR

(75) Inventors: Edward M. McKenna, Jr., Boulder, CO (US); David Besko, Thornton, CO (US)

(73) Assignee: COVIDIEN LP, Mansfield, MA (US)

( * ) Notice: Subject to any disclaimer, the term of this patent is extended or adjusted under 35 U.S.C. 154(b) by 1141 days.

(21) Appl. No.: 13/035,611

(22) Filed: Feb. 25, 2011

(65) Prior Publication Data

US 2012/0216335 A1    Aug. 30, 2012

(51) Int. Cl.
| | | |
|---|---|---|
| *A42B 1/24* | (2006.01) | |
| *A41D 13/12* | (2006.01) | |
| *A61B 1/24* | (2006.01) | |
| *A61F 13/00* | (2006.01) | |
| *A61F 13/42* | (2006.01) | |

(52) U.S. Cl.
CPC ............... *A41D 13/1281* (2013.01); *A61B 1/24* (2013.01); *A61F 13/00* (2013.01); *A61F 13/42* (2013.01); *A61F 13/00055* (2013.01)

(58) Field of Classification Search
CPC ............................. A42B 1/24; A61B 5/14551
USPC ................... 2/171, 171.4, 183, 413, 209.13; 600/309, 310, 311, 322, 323, 340, 344
See application file for complete search history.

(56) References Cited

U.S. PATENT DOCUMENTS

| | | | |
|---|---|---|---|
| 1,304,215 A | 5/1919 | Snyder | |
| 1,899,020 A | 2/1933 | Drueding | |
| 3,872,861 A | 3/1975 | Tamny et al. | |
| 4,035,846 A * | 7/1977 | Jencks | ................................ 2/413 |
| 4,321,930 A | 3/1982 | Jobsis et al. | |
| 5,040,540 A | 8/1991 | Sackner | |
| 5,217,013 A | 6/1993 | Lewis et al. | |
| 5,246,003 A | 9/1993 | DeLonzor | |
| 5,267,563 A | 12/1993 | Swedlow et al. | |
| 5,369,808 A | 12/1994 | Brewer et al. | |
| 5,431,170 A | 7/1995 | Mathews | |
| 5,465,714 A | 11/1995 | Scheuing | |
| 5,482,034 A | 1/1996 | Lewis et al. | |
| 5,496,257 A | 3/1996 | Kelly | |
| 5,507,752 A | 4/1996 | Elliott | |
| 5,584,296 A | 12/1996 | Cui et al. | |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Soto, D.; "A Comparative Study of Pulse Oximeter Measurements: Digit Versus Earlobe," Master of Science Thesis, California State University Dominguez Hills, May 1997, 46 pgs.

(Continued)

*Primary Examiner* — Tejash Patel
(74) *Attorney, Agent, or Firm* — Fletcher Yoder PC

(57) ABSTRACT

According to various embodiments, a medical device may include a hat and an annular securing device coupled to the hat and configured to adjustably secure the hat to a patient's body. The annular securing device may be configured to reduce in circumference when at least one end of the annular securing device is pulled in an axial direction. The medical device may also include a sensor disposed on the hat or annular securing device. The sensor may be configured to communicatively couple to the patient's body.

20 Claims, 5 Drawing Sheets

(56) References Cited

U.S. PATENT DOCUMENTS

| | | | |
|---|---|---|---|
| 5,817,008 | A | 10/1998 | Rafert et al. |
| 5,910,146 | A | 6/1999 | Alexander |
| 5,931,789 | A | 8/1999 | Alfano et al. |
| 5,995,857 | A | 11/1999 | Toomim et al. |
| 6,456,862 | B2 | 9/2002 | Benni |
| 6,553,242 | B1 | 4/2003 | Sarussi |
| 6,577,884 | B1 | 6/2003 | Boas |
| 6,615,065 | B1 | 9/2003 | Barrett et al. |
| 6,626,537 | B1 | 9/2003 | Odom et al. |
| 7,047,056 | B2 | 5/2006 | Hannula et al. |
| 7,582,109 | B2 | 9/2009 | De Legge et al. |
| 7,721,349 | B1 * | 5/2010 | Strauss .................................. 2/7 |
| 7,809,420 | B2 | 10/2010 | Hannula et al. |
| 7,813,779 | B2 | 10/2010 | Hannula et al. |
| 7,877,126 | B2 | 1/2011 | Hannula et al. |
| 7,877,127 | B2 | 1/2011 | Hannula et al. |
| 8,452,367 | B2 * | 5/2013 | Mannheimer et al. ........ 600/344 |
| 8,483,790 | B2 * | 7/2013 | Hannula et al. ................ 600/344 |
| 2002/0103520 | A1 | 8/2002 | Latham |
| 2002/0165462 | A1 | 11/2002 | Westbrook et al. |
| 2003/0109775 | A1 | 6/2003 | O'Neil et al. |
| 2003/0225323 | A1 | 12/2003 | Kiani et al. |
| 2003/0229276 | A1 | 12/2003 | Sarussi et al. |
| 2004/0018422 | A1 | 1/2004 | Islam et al. |
| 2005/0113655 | A1 | 5/2005 | Hull |
| 2005/0233707 | A1 | 10/2005 | Chen |
| 2006/0195028 | A1 | 8/2006 | Hannula et al. |
| 2006/0248946 | A1 | 11/2006 | Howell et al. |
| 2008/0143080 | A1 | 6/2008 | Burr |
| 2008/0173719 | A1 | 7/2008 | Wang |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| FR | 2685865 | 7/1993 |
| JP | 6014906 | 1/1994 |
| WO | WO9502358 | 1/1995 |
| WO | WO9736536 | 10/1997 |

OTHER PUBLICATIONS

Faisst, K., et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, A., et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, P., et al.; "An Integrated Pulse Oximeter System for Telemedicine Applications," *IEEE Instrumentation and Measurement Technology Conference*, Ottawa, Canada; May 19-21, 1997; pp. 102-104.

Dekock, M.; "Pulse Oximetry Probe Adhesive Disks: a Potential for Infant Aspiration," *Anesthesiology*, vol. 89, pp. 1603-1604 (1998).

Rhee, S., et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, B., et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Yang, B., et al.; "Development of the ring sensor for healthcare automation," *Robotics and Autonomous Systems*, vol. 30, pp. 273-281 (2000).

Rohling, R., et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Rhee, S., et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, S., et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, C.; "Design of a Pulse Oximetry Sensor Housing Assembly," California State University Master's Thesis, *UMI Dissertation Services*, UMI No. 1401306, (May 2000) 63 pages.

Yokota, N., et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, S., et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, F., et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gosney, S., et al.; "An alternative position for the pulse oximeter probe," *Anaesthesia*, vol. 56, p. 493 (2001).

Irie, A., et al.; "Respiration Monitors—Pulse Oximeters," *Neonatal Care*, vol. 15, No. 12, pp. 78-83 (2002) (Article in Japanese—contains English summary of article).

Shaltis, P., et al.; "Implementation and Validation of a Power-Efficient, High-Speed Modulation Design for Wireless Oxygen Saturation Measurement Systems," *IEEE*, pp. 193-194 (2002).

Warren, S., et al.; "Wearable Sensors and Component-Based Design for Home Health Care," *Proceedings of the Second Joint EMBS/BMES Conference*, Houston, Texas; Oct. 23-26, 2002; pp. 1871-1872.

Kyriacou, P. A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, D. et al.; "Measure Pressure with Thin Film," Paper Film & Foil Converter; May 1, 2003 (4 pages).

Avidan, A.; "Pulse oximeter ear probe," *Anaesthesia*, vol. 58, pp. 726 (2003).

Mannheimer, P., et al.; "The influence of Larger Subcutaneous Blood Vessels on Pulse Oximetry," *Journal of clinical Monitoring and Computing*, vol. 18, pp. 179-188 (2004).

Wendelken, S., et al.; "The Feasibility of Using a Forehead Reflectance Pulse Oximeter for Automated Remote Triage," *IEEE*, pp. 180-181 (2004).

(56) References Cited

OTHER PUBLICATIONS

Sugino, S., et al.; "Forehead is as sensitive as finger pulse oximetry during general anesthesia," *Can J. Anesth.; General Anesthesia*, vol. 51, No. 5; pp. 432-436 (2004).

Kocher, S., et al.; "Performance of a Digital $PCO_2/SPO_2$ Ear Sensor," *Journal of Clinical Monitoring and Computing*, vol. 18, pp. 75-59 (2004).

Johnston, W., et al.; "Effects of Motion Artifacts on helmet-Mounted Pulse Oximeter Sensors," 2 pgs. (2004).

Branche, P., et al.; "Measurement Reproducibility and Sensor Placement Considerations in Designing a Wearable Pulse Oximeter for Military Applications," 2 pgs. (2004).

Heuss, L., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Hayoz, J., et al.; "World's First Combined digital Pulse Oximetry Pulse Oximetry and Carbon Dioxide Tension Ear Sensor", *Abstracts*, A6, p. S103. (undated).

http://www.cfw.com.my/fujifilm.html (4 pages).

Dresher, R., in "Wearable Forehead Pulse Oximetry: Minimization of Motion and Pressure Artifacts" A Thesis Submitted to the Faculty of the Worcester Polytechnic Institute in partial fulfillment of the requirements for the Degree of Master of Science, May 3, 2006, p. 1-93.

* cited by examiner

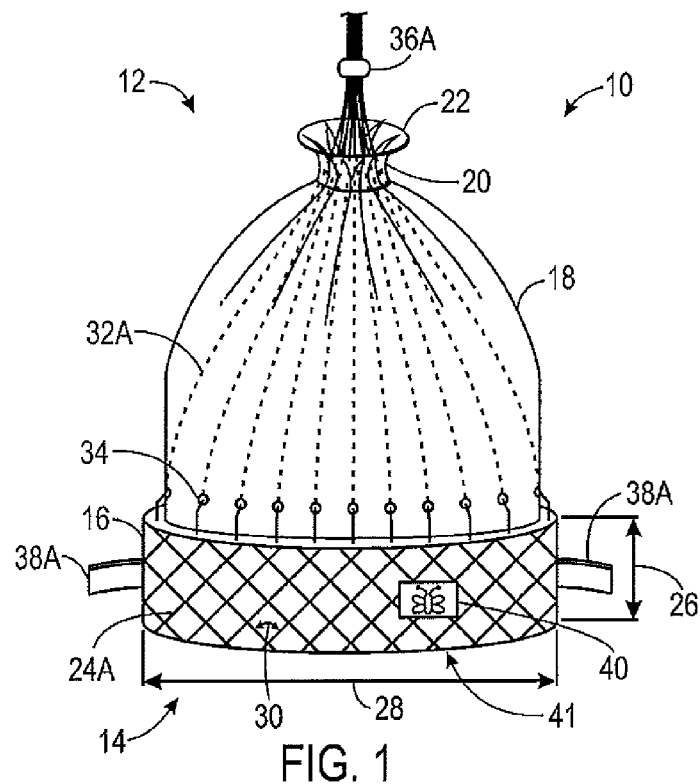
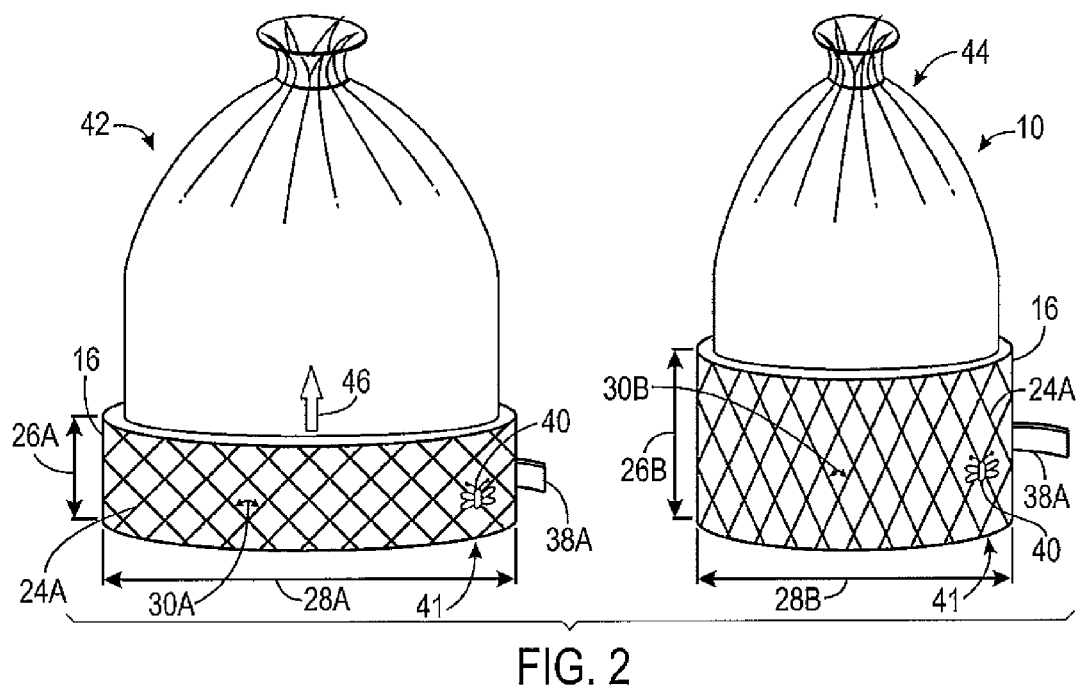

DEVICE FOR SECURING A MEDICAL SENSOR

BACKGROUND

The present disclosure relates generally to medical sensors and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Many types of medical sensors, such as optical sensors, are used to measure physiological characteristics of a patient. Typically, an optical sensor provides emitted light, which is then scattered through a portion of a tissue of a patient and detected. Various characteristics of a patient can be determined from analyzing such light, such as oxygen saturation, pulse rate, tissue bilirubin, and so forth.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor, which scatters light through a portion of the tissue of the patient where blood perfuses the tissue, and photoelectrically senses the absorption of light in such tissue. The amount of light absorbed and/or scattered is then used to calculate the amount of blood constituent being measured.

The light transmitted through the tissue is selected to be of one or more wavelengths that are absorbed by the blood in an amount representative of the amount of the blood constituent present in the blood. The amount of transmitted light scattered through and/or absorbed by the tissue will vary in accordance with the changing amount of blood constituent in the tissue. For measuring blood oxygen level, such sensors have typically been provided with a light source that is adapted to generate light of at least two different wavelengths, in accordance with known techniques for measuring blood oxygen saturation.

Known non-invasive sensors include devices that are secured to a portion of the body, such as a finger, an ear, or the scalp. In animals and humans, the tissue of these body portions is perfused with blood and the tissue surface is readily accessible to the sensor. More particularly, certain types of oximeter sensors are applied to a forehead of the patient. For example, an oximeter sensor attached to the inside of a stocking hat provides one technique for placing, retaining, and locating the sensor on a forehead of an infant. Such hats should fit securely on the head of the infant to help the sensor stay in contact with the tissue and apply an optimal pressure to the forehead. Indeed, measurement accuracy may diminish because of venous pulsations and/or less than optimal sensor contact caused by a loose hat or a hat that slips off the forehead.

BRIEF DESCRIPTION OF THE DRAWINGS

Advantages of the disclosed techniques may become apparent upon reading the following detailed description and upon reference to the drawings in which:

FIG. 1 illustrates a perspective view of an example of a hat structure for holding a pulse oximetry sensor on a tissue of a patient using an annular securing device incorporated into the hat;

FIG. 2 illustrates a perspective view of an example of a hat pulse oximetry sensor before and after being tightened;

DETAILED DESCRIPTION OF SPECIFIC EMBODIMENTS

Figure 3:
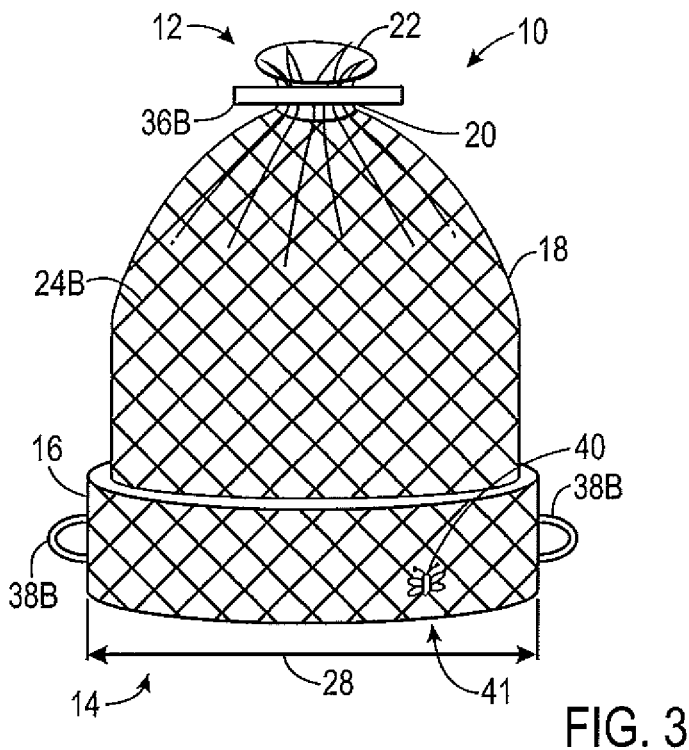
FIG. 3 illustrates a perspective view of an example of a hat pulse oximetry sensor with an annular securing device incorporated into most of the hat.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Sensors for pulse oximetry or other applications utilizing spectrophotometry may include the use of an annular securing device to retain a sensor structure on a patient. For example, the annular securing device may be used in a stocking hat to secure the pulse oximetry sensor on a head of the patient. The annular securing device may be similar to that used in toys referred to as Chinese finger traps, Chinese finger puzzles, Chinese handcuffs, and so forth. Pulling on one or both ends of the annular securing device in an axial direction may reduce the circumference and diameter of the annular securing device. Thus, the annular securing device may be used in the stocking hat to tighten and conform the stocking hat to the patient, thereby applying a predictable pressure on the sensor. As discussed below, the ability of the hat to adapt to different head sizes enables an optimal pressure to be applied by the sensor to the head of the patient. Use of various adjustment devices attached to the annular securing device may facilitate adjustment of the diameter of the hat. In one embodiment, a locking or restraining device may be provided to maintain a desired diameter of the hat. In another embodiment, indicia on the hat may be used to indicate positions of the adjustment devices corresponding to particular head sizes. In one embodiment, removal devices may be provided on the hat to facilitate removal of the hat. Thus, a caregiver may be able to remove and reapply the hat quickly, saving time for the caregiver. In further embodiments, the caregiver may place the sensor structure on other areas of the patient including, but not limited to, a finger, a foot, or a limb.

With the foregoing in mind, FIG. 1 is a drawing of an adjustable stocking hat 10 in accordance with an embodiment. As described in detail below, the stocking hat 10 includes an annular securing device 24A that enables the stocking hat 10 to conform to a variety of head sizes. In this example, the stocking hat 10 includes openings at a distal end 12 and a proximal end 14. The annular securing device 24A is located in a headband portion 16 of the stocking hat 10. As illustrated, the annular securing device 24A may be integral to the stocking hat 10, such that it is inserted into a pocket formed around the periphery of the stocking hat 10. An upper portion 18 of the stocking hat 10 is located above the headband portion 16. Located near the distal end 12 of the stocking hat 10 is a constriction 20, which is smaller than the opening at the proximal end 14. Located adjacent to the constriction is a distal opening 22 through which cables, wires, strings, and so forth may pass therethrough. For example, as described in detail below, a sensor cable or an adjustment device for the annular securing device 24A may pass through the distal opening 22 to help direct the cable or device away from the face of patient.

In the illustrated embodiment, when one or both ends of the annular securing device 24A are pulled toward the distal end 12 or the proximal end 14 (i.e. in an axial direction), the height 26 of the annular securing device 24A increases and its diameter 28 and circumference decrease. In certain embodiments, the annular securing device 24A may be constructed from a cylindrical, helically wound braid or a common biaxial braid. For example, the annular securing device 24A may be constructed by weaving together two perpendicular groups of strands referred to as a warp and a weft. The warp refers to the set of lengthwise strands and the weft refers to the strands inserted over and under the strands of the warp. The strands of the warp and weft may be free to move pass one another. The increase in the height 26 of the annular securing device 24A is obtained by reducing an angle 30 between the warp and weft strands at their crossing points, which reduces the diameter 28 and hence, the overall circumference of the annular securing device 24A. Additional pulling of the ends of the annular securing device 24A causes the circumference and the diameter 28 of the annular securing device 24A to further decrease. The strands of the annular securing device 24A may be made from materials such as, but not limited to, fabrics, cloths, wood, plastic, metal, and so forth. For example, in certain embodiments, the strands may be cloth strips with a width greater than approximately 0.5 cm.

In the illustrated embodiment, adjustment devices 32A may be attached to the annular securing device 24A to enable the caregiver to pull the annular securing device 24A in an axial direction to reduce the circumference of the stocking hat 10. In certain embodiments, the adjustment devices 32A may be attached to individual strands of the annular securing device 24A. In other embodiments, the adjustment devices 32A may be attached to an annular ring or similar structure attached to the strands of the annular securing device 24A. In the illustrated embodiment, the adjustment devices 32A are strings and are spaced evenly about the annular securing device 24A. In other embodiments, the spacing of the adjustment devices 32A may not be regular. In addition, the number of adjustment devices 32A may be selected based on the size of the stocking hat 10, the amount of force needed to pull on the annular securing device 24A, the strength of the annular securing device 24A, adjustment devices 32A, or connection between the annular securing device 24A and adjustment devices 32A, and so forth. Further, the adjustment devices 32A may include, but are not limited to, strings, threads, filaments, twine, cords, cables, straps, strips, bands, belts, and so forth. The adjustment devices 32A may be made from natural materials, such as, but not limited to, cotton, linen, hemp, and so forth or synthetic fibers such as, but not limited to, polypropylene, nylon, polyesters, polyethylene, and so forth.

As shown in FIG. 1, proximal ends 14 of the adjustment devices 32A may be located externally to the stocking hat 10. The adjustment devices 32A pass through openings 34 in the stocking hat 10 and upper portions of the adjustment devices 32A, indicated by dashed lines in FIG. 1, are located internally to the stocking hat 10. Such a configuration of the adjustment devices 32A may provide a more pleasing appearance for the stocking hat 10 by reducing the visibility of the adjustment devices 32A. In addition, by routing a portion of the adjustment devices 32A internally to the stocking hat 10, the potential for the patient to contact the adjustment devices 32A is reduced. In other embodiments, the adjustment devices 32A may be routed completely internally to the stocking hat 10.

The adjustment devices 32A may come together near the distal opening 22 and are routed outside of the stocking hat 10. Thus, all of the adjustment devices 32A may be pulled simultaneously to tighten the annular securing device 24A evenly. In an embodiment, the adjustment devices 32A may be constrained in the stocking hat 10 to avoid interfering with the eyesight of the patient or bothering the patient. A locking device 36A may be disposed on the adjustment devices 32A near the distal opening 22. After the adjustment devices 32A are pulled toward the distal end 12, such that the annular securing device 24A is tightened to the desired diameter 28, the locking device 36A may be slid toward the proximal end 14 and against the constriction 20 to maintain the adjustment devices 32A in the desired position. Until the locking device 36A is removed, the stocking hat 10 may remain at the desired diameter 28 for extended periods of time. The locking device 36A may be a clip or similar device that uses friction or another restraining force to help prevent the adjustment devices 32A from moving toward the proximal end 14, thereby loosening the annular securing device 24A. To remove the stocking hat 10 from the patient, the locking device 36A may be disengaged or moved away from the stocking hat 10, thereby enabling the adjustment devices 32A to move toward the proximal end 14.

Alternatively, the stocking hat 10 may include one or more removal devices 38A to enable removal of the stocking hat 10 from the patient. Specifically, the removal devices 38A shown in FIG. 1 may be configured as one or more tabs disposed about the perimeter of the annular securing device 24A. By pulling outward on the removal devices 38A away from the annular securing device 24A, the diameter 28 of the stocking hat 10 may be increased enough to enable the stocking hat 10 to slide off the patient. The removal devices 38A may be made from materials similar to those used for the annular securing device 24A or the stocking hat 10.

The stocking hat 10 may also include one or more sensor indicia 40 corresponding to the location of one or more underlying sensors 41. As described in detail below, the sensor 41 is disposed on an inner surface of the stocking hat 10 and thus, is not visible in FIG. 1. The sensor 41 may be a pulse oximetry sensor, or any other type of sensor that may be disposed in the stocking hat 10. The sensor indicia 40 may be placed on a patch that is attached to the stocking hat 10, may be attached directly to the stocking hat 10, or may be printed on the stocking hat 10. The sensor indicia 40 facilitate proper placement of the stocking hat 10 and thus the sensor 41 on the head of the patient. Therefore, coupling the sensor 41 with the stocking hat 10 allows for easy placement of the sensor 41 on the head of the patient while applying a predictable pressure on the sensor 41 using the annular securing device 24A.

Although the annular securing device 24A is shown exposed in FIG. 1, it may also be covered. For example, the annular securing device 24A may be disposed between two layers of fabric that form the inside and outside surfaces of the stocking hat 10. Such a configuration would help prevent the patient from contacting the annular securing device 24A. For example, such a configuration of the stocking hat 10 may help protect the annular securing device 24A from damage or interference by the patient or other medical equipment. In addition, covering the annular securing device 24A may provide a more pleasing appearance for the stocking hat 10.

To illustrate how the stocking hat 10 appears before and after placement on the head of a patient, FIG. 2 shows drawings of the stocking hat 10 and how the shape and dimensions of the stocking hat 10 change after the annular securing device 24A is tightened. On the left-hand side of FIG. 2, the stocking hat 10 is shown in a relaxed or loosened state 42. On the right-hand side of FIG. 2, the stocking hat 10 is shown in a tightened state 44. To change the stocking hat 10 from the relaxed state 42 to the tightened state 44, the top of the annular securing device 24A is pulled in the direction of arrow 46, which may be accomplished using any of the adjustment devices 32 described herein. In the relaxed state 42, the stocking hat 10 has a relaxed height 26A and a relaxed diameter 28B. In the tightened state 44, the stocking hat 10 has a tightened height 26B and a tightened diameter 28B. As shown in FIG. 2, the tightened height 26B is greater than the relaxed height 26A and the tightened diameter 28B is less than the relaxed diameter 28B. Thus, by increasing the height 26 of the annular securing device 24A, the diameter 28 of the annular securing device 24A decreases, thereby conforming and securing the stocking hat 10 to the patient. As shown in FIG. 2, the angle 30 between the warp and weft strands changes as the stocking hat 10 is tightened. Specifically, a relaxed angle 30A is greater than a tightened angle 30B. In other words, as the angle 30 between the warp and weft strands decreases, the height 26 of the stocking hat 10 increases and the diameter 28 decreases.

The annular securing device 24A need not be limited to the headband portion 16 of the stocking hat 10. For example, FIG. 3 is a drawing of an embodiment of the stocking hat 10 in which the annular securing device 24B is located in both the headband portion 16 and the upper portion 18. Thus, when the caregiver pulls the distal end 12 of the stocking hat 10 in an axial direction, the headband portion 16 and upper portion 18 of the stocking hat 10 tighten and conform to the head of the patient. In other words, substantially the entire the stocking hat 10 conforms to the patient. With such a configuration, the stocking hat 10 may be less likely to be inadvertently removed or dislodged. For example, the annular securing device 24B may be useful when used with neonates.

After pulling on the distal end 12 of the stocking hat 10 shown in FIG. 3, the caregiver may then fasten the locking device 36B adjacent to the constriction 20 against the top of the head. The locking device 36B may be a clip that includes a plurality of small grips to enable the locking device 36B to grab the annular securing device 24B. Once the locking device 36B is fastened in place, both the locking device 36B and the constriction 20 may be unable to move any further toward the proximal end 14 because of the placement of the locking device 36B against the head. Thus, the locking device 36B helps to prevent the annular securing device 24B from relaxing, thereby maintaining the desired diameter 28 of the stocking hat 10. In other embodiments, the locking device 36B may be a rubber band or other similar device to maintain the desired diameter 28 of the stocking hat 10. To remove the stocking hat 10 from the patient, the locking device 36B is removed and the distal end 12 of the stocking hat 10 is allowed to relax toward the patient, thereby loosening the stocking hat 10. Alternatively, the stocking hat 10 may include one or more removal devices 38B attached to the perimeter of the headband portion 16. In FIG. 3, the removal devices 38B are configured as loops that may be used in a manner similar to the removal devices 38A shown in FIG. 1. Specifically, the caregiver may insert a finger into the removal device 38B and pull outward and away from the patient to enable removal of the stocking hat 10 without causing the stocking hat 10 to tighten.

Figure 4:
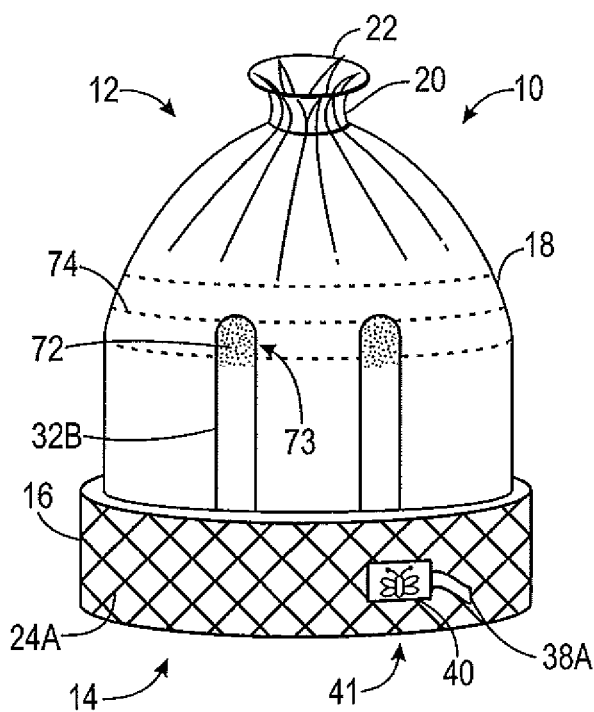
FIG. 4 illustrates a perspective view of an example of a hat pulse oximetry sensor with an annular securing device incorporated into a band of the hat.

Other methods may be used to maintain the diameter 28 of the stocking hat 10. For example, FIG. 4 shows a drawing of the stocking hat 10 in which one or more adjustment devices 32B may be attached to the annular securing device 24A and pulled in an axial direction to tighten the annular securing device 24A and reduce the diameter of the stocking hat 10. The adjustment devices 32B are configured as tabs or strips attached to individual strands of the annular securing device 24A or to a ring or similar structure attached to the strands of the annular securing device 24A. The number of adjustment devices 32B may be less than that of the adjustment devices 32A shown in FIG. 1 because the adjustment devices 32B may be wider and stronger. In addition, the manufacture of stocking hats 10 using the adjustment devices 32B may be less complicated and/or less costly than that of stocking hats 10 using the adjustment devices 32A shown in FIG. 1. Further, the adjustment devices 32B may be less likely to be interfered with by the patient. The distal ends 12 of the adjustment devices 32B include a hook side 72 of a hook and loop fastener. The upper portion 18 of the stocking hat 10 may include a loop side 73 of the hook and loop fastener opposite the hook side 72. Alternatively, the material used for the stocking hat 10 may function as the loop side 73 of the hook and loop fastener. To tighten the annular securing device 24A, the adjustment devices 32B are pulled in the direction of the distal end 12 of the stocking hat 10 and the hook sides 72 fastened to the loop sides 73. Correspondingly, to loosen the annular securing device 24A, the hook sides 72 of the adjustment devices 32B are removed from the loop sides 73. The adjustment devices 32B may be made from materials similar to those used for the stocking hat 10.

In the illustrated embodiment, one or more adjustment indicia 74 may be provided on the upper portion 18 of the stocking hat 10. The adjustment indicia 74 may include, but are not limited to, lines, marks, symbols, and so forth, to correspond to one or more head sizes of the patients using the stocking hat 10. For example, adjustment indicia 74 located near the proximal end 14 may correspond to larger head sizes and adjustment indicia 74 located near the distal end 12 may correspond to smaller head sizes. Thus, the adjustment indicia 74 may facilitate tightening the stocking hat 10 to exert the proper pressure on the pulse oximeter sensor 41 for a particular patient. In other embodiments, part of the upper portion 18 of the stocking hat 10 may also include the annular securing device 24B. In such embodiments, the adjustment devices 32B may be attached to the top of the annular securing device 24B located in the upper portion 18. In further embodiments, devices such as, but not limited to, snaps, buttons, and other fasteners, may be used to secure the adjustment devices 32B to the stocking hat 10.

As shown in FIG. 4, the removal device 38A may be attached to part of the sensor index 40. Such a location for the removal device 38A may enable the caregiver to locate the removal device 38A quicker. In addition, it may be simpler to attach the removal devices 38A to the sensor indicia 40 instead of directly to the annular securing device 24A. In certain embodiments, the sensor indicia 40 may include raised components that enable the sensor indicia 40 to function as the removal devices 38. Specifically, a caregiver may be able to grasp the raised component of a sensor index 40 to remove the stocking hat 10 without causing the annular securing device 24A to tighten. In other embodiments, one or more removal devices 38B, such as the loops shown in FIG. 3, may be attached to the sensor indicia 40 or the headband portion 16 to facilitate removal of the stocking hat 10.

Figure 5:
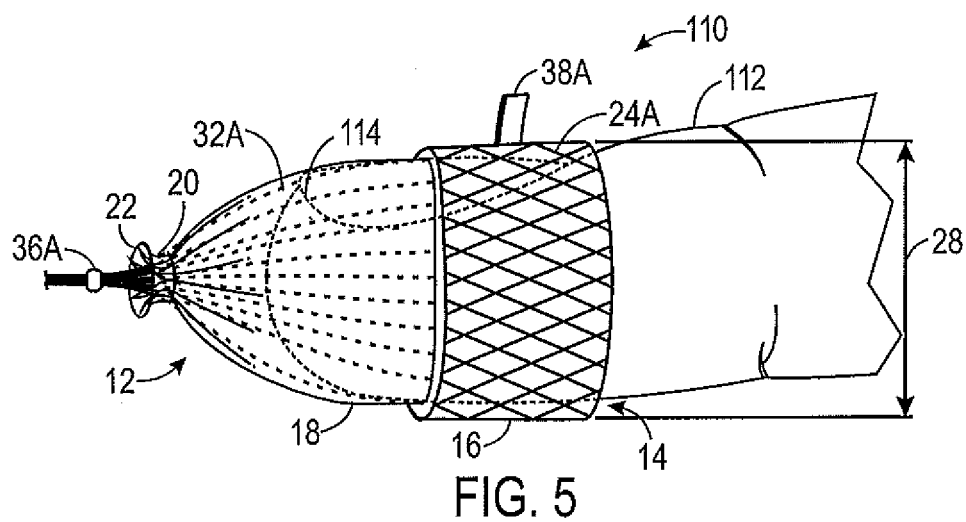
FIG. 5 illustrates a perspective view of an example of a finger pulse oximetry medical device.

The head of the patient is not the only location where the pulse oximetry sensor 41 may be placed. For example, FIG. 5 shows a drawing of a finger pulse oximetry medical device 110 disposed on a finger 112 of a patient. The sensor 41 may be placed on the finger 112 when the head is injured, to avoid patient discomfort, or to reduce the possibility of inadvertent removal. The medical device 110 is constructed and operated in a manner similar to the stocking hat 10 described in detail above. Specifically, the band portion 16 of the medical device 110 may include the annular securing device 24A and the pulse oximetry sensor 41. One or more adjustment devices 32A may be attached to the annular securing device 24A, routed through the constriction 20, and exit through the distal opening 22. When the adjustment devices 32A are pulled away from the finger 112, the diameter 28 of the medical device 110 decreases, conforming the medical device 110 to the finger 112. In the illustrated embodiment, the adjustment devices 32A are routed completely through the interior of the medical device 110. Furthermore, the locking device 36A may be used to secure the annular securing device 24A in a tightened position around the finger 112. In the illustrated embodiment, the band portion 16 may be positioned away from a nail 114 of the finger 112 to enable more accurate pulse oximetry measurements. The medical device 110 may be released from the finger 112 be either removing the locking device 36A or pulling on the removal devices 38A in a direction away from the finger 112. In other embodiments, the medical device 110 may be positioned on a toe of the patient. In further embodiments, the medical device 110 may include the annular securing device 24B and locking device 36B such that generally all of the medical device 110 is conformable to the finger 112. Such a configuration may reduce the possibility of inadvertent removal of the medical device 110.

Figure 6:
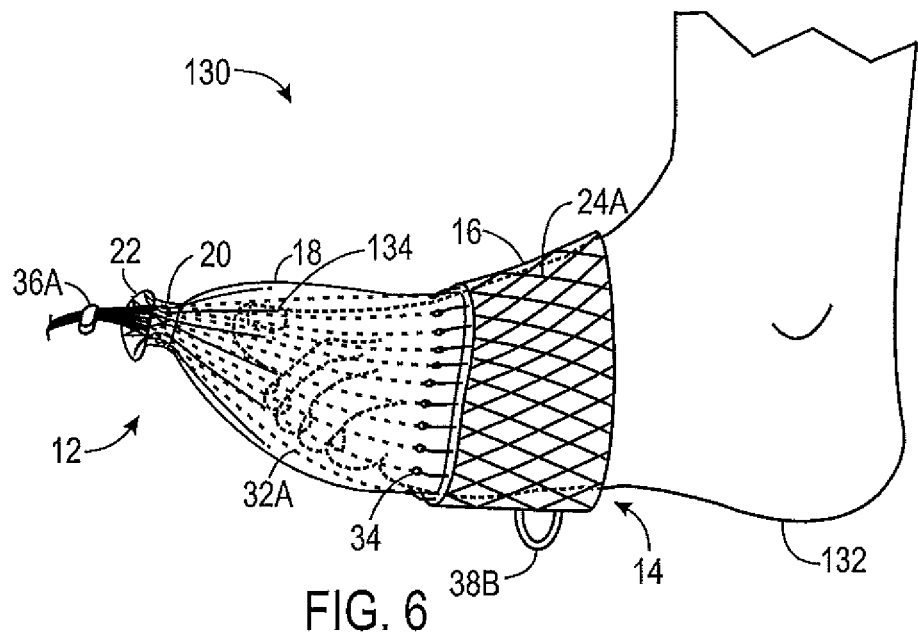
FIG. 6 illustrates a perspective view of an example of a foot pulse oximetry medical device.

Other than the head, finger, and toe of the patient, the pulse oximetry sensor 41 may also be placed on a foot 132. In FIG. 6, the band portion 16 of a foot pulse oximetry medical device 130 may include the annular securing device 24A. Placing the medical device 130 on the foot 132 may be useful if other locations are unavailable, injured, or inconvenient for the patient. In the illustrated embodiment, the medical device 130 is similar to the stocking hat 10 described in FIG. 1. Specifically, pulling on the adjustment devices 32A away from the foot 132 results in a decrease in the diameter 28 of the medical device 130, conforming the medical device 130 to the foot 132. In other embodiments the medical device 130 may be configured similar to the stocking hats 10 shown in FIG. 3 or 4. In the illustrated embodiment, the medical device 130 covers a foot 132 of the patient instead of being disposed on individual toes 134. In addition, the medical device 130 uses removal devices 38B configured as loops as one option for removing the medical device 130 from the foot 132. In other embodiments, pulling on tabs, such as removal devices 38A, or removal of the locking device 36A may be used to remove the medical device 130.

Figure 7:
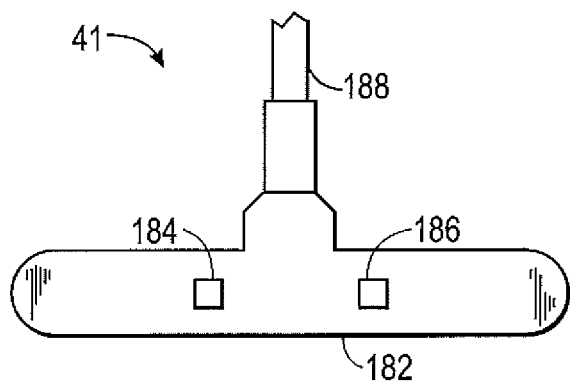
FIG. 7 illustrates a perspective view of an example of a pulse oximetry sensor body.

Turning next to the pulse oximetry sensor 41, a reflectance-type pulse oximetry sensor 41, as shown in FIG. 7, may be placed or adhered to the inside of the stocking hat 10. Examples of such a sensor 41 and its use and construction may be found in U.S. Pat. No. 7,047,056, which issued on May 16, 2006, as well as U.S. Pat. No. 7,809,420, which issued on Oct. 5, 2010, which are both herein incorporated by reference in their entirety for all purposes. The sensor 41 may include a substrate 182 that may be made from any suitable material. In an embodiment, the substrate 182 is a foam or other conformable material. In one embodiment, the substrate 182 is black or dark in color to absorb stray light and minimize any shunting of light between the sensor 41 and the patient skin. In one embodiment, the substrate 182 may include an adhesive material to secure the sensor 41 directly to the tissue. In one embodiment, the sensor 41 may include an emitter 184 containing emitters for two or more wavelengths of lights and a detector 186 spaced apart from the emitter 184.

Also shown in FIG. 7 is a cable 188 for providing drive current to the emitter 184, and providing the detector signal to a medical device. In addition to providing the electrical connection to the downstream medical device, the cable 188 may provide shielding to protect the small signals from the detector 186 against external electrical interference. In addition, the sensor 41 may include suitable structures for providing electrical connections to the cable 188 and/or downstream medical device, such as a flex circuit, a Faraday shield, and leads connecting the optical components of the sensor 41 to the electrical components.

Figure 8:
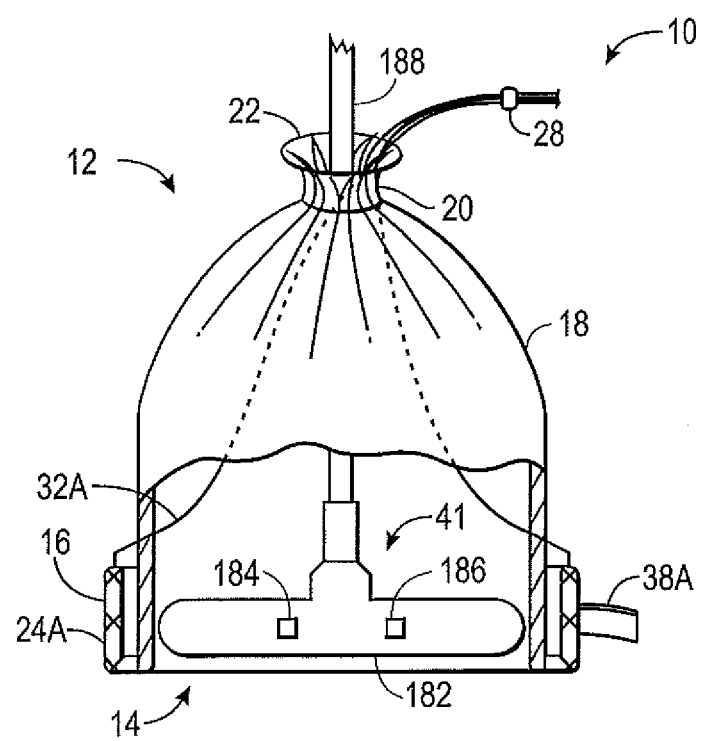
FIG. 8 illustrates a partial cross-sectional view of an example of a hat pulse oximetry sensor.

The sensor assembly 41 is shown fully assembled together with the stocking hat 10 in FIG. 8. As shown, the sensor 41 is positioned on the interior of the stocking hat 10 such that the emitter 184 and detector 186 may come into contact with the skin when the stocking hat 10 is applied to the patient. The sensor 41 may be attached (e.g., adhered or sewn into) to the inside band of the stocking hat 10. In one embodiment, the stocking hat 10 may include indicators, such as the sensor indicia 40 described above, to position the sensor 41 on a particular location on the forehead of the patient, for example to position the sensor 41 on the lower forehead region, above the eyebrow, with the sensor optics (emitter 184 and detector 186) located above and predominantly lateral to or centered over the iris. The location of the reflectance sensor 41 in the stocking hat 10 allows appropriate placement of the sensor 41 in the desired forehead location by a user not skilled in sensor placement. FIG. 8 shows that the cable 188 is positioned through the distal opening 22 in the top of the stocking hat 10. In an embodiment, the cable 188 may be adhered or otherwise constrained in the stocking hat 10 so that the cable 188 generally is positioned away from the sensor 41 to avoid interfering with the eyesight of the patient or bothering the patient.

Figure 9:
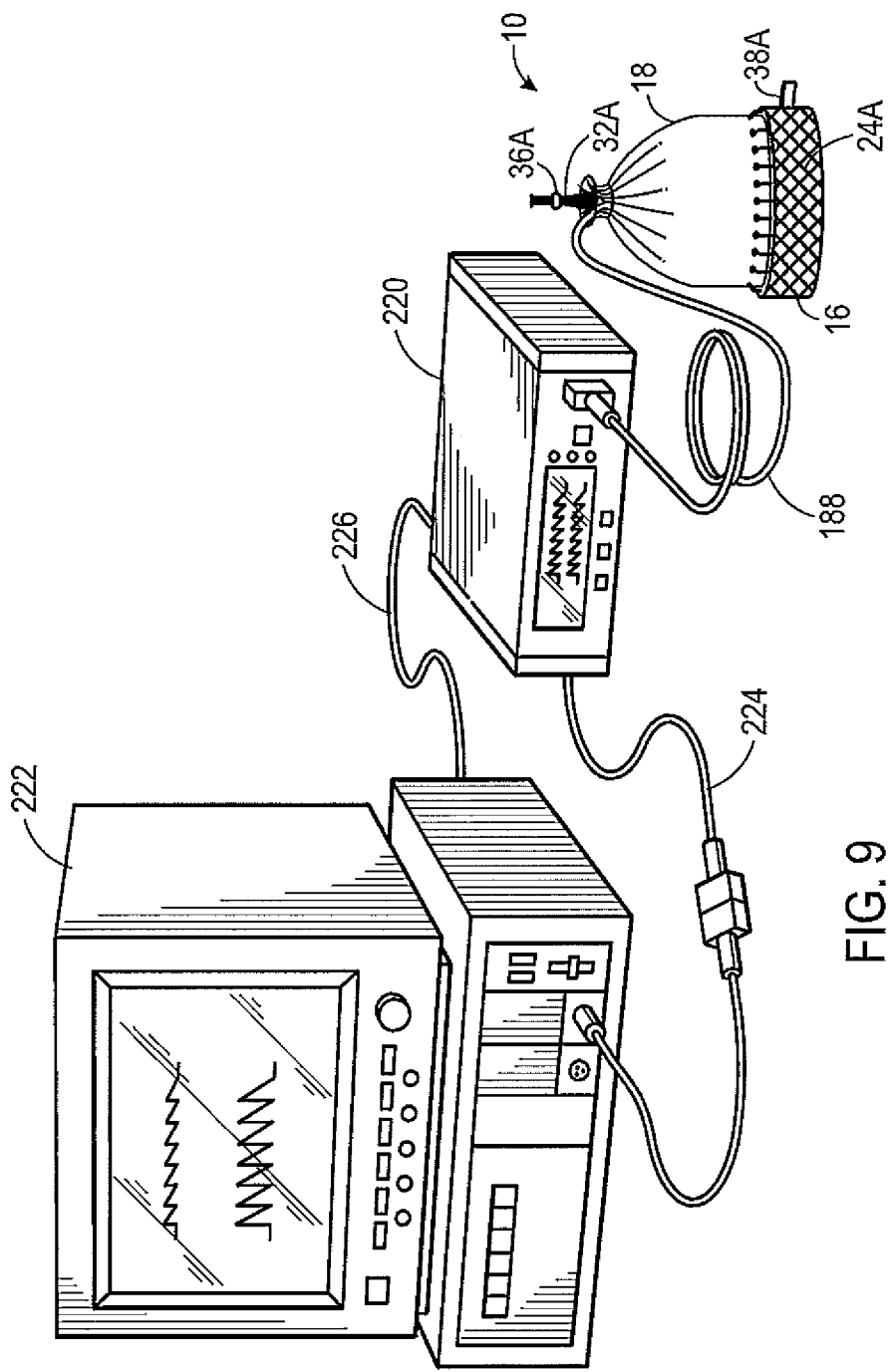
FIG. 9 illustrates an example of a pulse oximetry system coupled to a multi-parameter patient monitor and a sensor.

A sensor or sensor assembly, illustrated generically as the stocking hat 10, may be used in conjunction with a pulse oximetry monitor 220, as illustrated in FIG. 9. It should be appreciated that the cable 188 of the stocking hat 10 may be coupled to the monitor 220 or it may be coupled to a transmission device to facilitate wireless transmission between the stocking hat 10 and the monitor 220. The monitor 220 may be any suitable pulse oximeter, such as those available from Nellcor Puritan Bennett LLC. Furthermore, to upgrade conventional pulse oximetry provided by the monitor 220 to provide additional functions, the monitor 220 may be coupled to a multi-parameter patient monitor 222 via a cable 224 connected to a sensor input port or via a cable 226 connected to a digital communication port.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A medical device comprising:
   a hat;
   an annular securing device coupled to the hat and configured to adjustably secure the hat to a patient's body, wherein the annular securing device is configured to reduce in circumference when at least one end of the annular securing device is pulled in an axial direction;
   a locking device configured to maintain the circumference of the annular securing device when the locking device is locked; and
   a sensor disposed on the hat or annular securing device, wherein the sensor is configured to communicatively couple to the patient's body.

2. The medical device of claim 1, comprising:
   a plurality of adjustment devices coupled to the annular securing device, wherein the plurality of adjustment devices are configured to reduce the circumference of the annular securing device when the plurality of adjustment devices are pulled in an axial direction relative to the annular securing device, to at least partially route through an interior of the hat, to extend from the annular securing device through an open portion of the hat configured to be proximate to a top of the hat when the hat is applied to the patient's body, and wherein the annular securing device is disposed in a band of the hat;
   wherein the locking device is coupled to the plurality of adjustment devices proximate to the top of the hat, wherein the locking device is configured to maintain the circumference of the annular securing device when the locking device is locked; and
   a removal device coupled to the band of the hat or annular securing device, wherein the removal device is configured to increase the circumference of the annular securing device.

3. The medical device of claim 1, comprising:
   wherein the locking device is coupled to a top of the hat, wherein the locking device is configured to maintain the circumference of the annular securing device when the locking device is locked, and wherein the annular securing device is disposed throughout the hat; and
   a removal device coupled to the hat or the annular securing device, wherein the removal device is configured to increase the circumference of the annular securing device.

4. The medical device of claim 1, comprising:
   a plurality of adjustment devices coupled to the annular securing device, wherein the plurality of adjustment devices are configured to reduce the circumference of the annular securing device when the plurality of adjustment devices are pulled in an axial direction relative to the annular securing device, and wherein the annular securing device is disposed in a band of the hat;
   wherein the locking device comprises a hook and loop fastener, wherein a first portion of the fastener is coupled to the plurality of adjustment devices, the hat comprises a second portion of the fastener or the second portion is disposed on the hat, and the fastener is configured to maintain the circumference of the annular securing device when the first and second portions of the loop fastener are fastened;
   an adjustment index disposed on the hat or the annular securing device, wherein the adjustment index is configured to indicate whether the annular securing device is properly securing the hat to the patient; and
   a removal device coupled to the band of the hat or the annular securing device, wherein the removal device is configured to increase the circumference of the annular securing device.

5. The medical device of claim 1, wherein the annular securing device comprises a cylindrical, helically wound braid or a cylindrical biaxial braid.

6. The medical device of claim 1, wherein the annular securing device comprises interwoven warp strands and weft strands.

7. The medical device of claim 1, wherein the sensor comprises a substrate disposed on the hat or annular securing device, an emitter disposed on the substrate, a detector disposed on the substrate, and a cable coupled to the emitter and the detector.

8. The medical device of claim 1, comprising a plurality of adjustment devices coupled to the annular securing device, wherein the plurality of adjustment devices are configured to reduce the circumference of the annular securing device when the plurality of adjustment devices are pulled in an axial direction relative to the annular securing device.

9. The medical device of claim 8, wherein the plurality of adjustment devices comprise strings, threads, filaments, twine, cords, cables, straps, strips, bands, or belts, or any combination thereof.

10. The medical device of claim 1, wherein the locking device comprises a clip or a hook and loop fastener, or any combination thereof.

11. The medical device of claim 1, wherein the hat comprises a neonatal stocking cap.

12. A method of operating a medical device, comprising:
    applying a hat to a patient's body, wherein an annular securing device is coupled to the hat, and wherein a sensor is disposed on the hat or annular securing device;
    pulling at least one end of the annular securing device in an axial direction to reduce a circumference of the annular securing device, such that the sensor is communicatively coupled to the patient's body; and
    placing a locking device on the hat or a plurality of adjustment devices coupled to the annular securing device to maintain the circumference of the annular securing device.

13. The method of claim 12, comprising pulling a plurality of adjustment devices coupled to the annular securing device to reduce the circumference of the annular securing device.

14. The method of claim 12, comprising increasing the circumference of the annular securing device with a removal device coupled to the hat or annular securing device to remove the hat from the patient's body.

15. A method of manufacturing a medical device, comprising:
    providing an annular securing device on a hat, wherein the annular securing device is configured to adjustably secure the hat to a patient's body and to reduce in circumference when at least one end of the annular securing device is pulled in an axial direction;
    providing a sensor on the hat or annular securing device, wherein the sensor is configured to communicatively couple to the patient's body;

assembling the hat, annular securing device, and sensor to form the medical device;

providing a plurality of adjustment devices on the annular securing device, wherein the plurality of adjustment devices are configured to reduce the circumference of the annular securing device when the plurality of adjustment devices are pulled in an axial direction relative to the annular securing device;

providing a locking device on the hat or the plurality of adjustment devices, wherein the locking device is configured to maintain the circumference of the annular securing device when the locking device is locked; and providing a removal device coupled to the hat or the annular securing device, wherein the removal device is configured to increase the circumference of the annular securing device.

16. The method of claim 15, comprising providing the annular securing device in a band of the hat.

17. The method of claim 15, comprising providing the annular securing device throughout the hat.

18. The medical device of claim 1, wherein the sensor comprises a pulse oximetry sensor.

19. The method of claim 12, wherein the sensor comprises a pulse oximetry sensor.

20. The method of claim 15, wherein the sensor comprises a pulse oximetry sensor.

* * * * *